United States Patent
Uber, III

(10) Patent No.: US 11,576,985 B2
(45) Date of Patent: Feb. 14, 2023

(54) CONTRAST IMAGING AGENT WITH DISSOLVED GAS-EVOLVING FLUID

(71) Applicant: BAYER HEALTHCARE LLC, Whippany, NJ (US)

(72) Inventor: Arthur Uber, III, Pittsburgh, PA (US)

(73) Assignee: BAYER HEALTHCARE LLC, Whippany, NJ (US)

(*) Notice: Subject to any disclaimer, the term of this patent is extended or adjusted under 35 U.S.C. 154(b) by 106 days.

(21) Appl. No.: 16/940,601

(22) Filed: Jul. 28, 2020

(65) Prior Publication Data

US 2020/0353103 A1 Nov. 12, 2020

Related U.S. Application Data

(62) Division of application No. 15/551,469, filed as application No. PCT/US2016/018707 on Feb. 19, 2016, now abandoned.

(60) Provisional application No. 62/118,946, filed on Feb. 20, 2015, provisional application No. 62/118,517, filed on Feb. 20, 2015.

(51) Int. Cl.
| | |
|---|---|
| *A61K 49/04* | (2006.01) |
| *A61B 6/03* | (2006.01) |
| *A61B 6/00* | (2006.01) |
| *A61M 5/00* | (2006.01) |
| *A61B 5/055* | (2006.01) |
| *A61B 8/08* | (2006.01) |

(52) U.S. Cl.
CPC ............ *A61K 49/0447* (2013.01); *A61B 6/00* (2013.01); *A61B 6/032* (2013.01); *A61B 6/481* (2013.01); *A61K 49/04* (2013.01); *A61K 49/0433* (2013.01); *A61M 5/007* (2013.01); *A61B 5/055* (2013.01); *A61B 6/037* (2013.01); *A61B 8/481* (2013.01); *A61M 2210/1039* (2013.01)

(58) Field of Classification Search
CPC ............ A61K 49/0447; A61K 49/0433; A61K 49/04; A61B 6/032; A61B 6/481; A61B 6/00; A61B 5/055; A61M 5/007
See application file for complete search history.

(56) References Cited

U.S. PATENT DOCUMENTS

| | | |
|---|---|---|
| 3,975,512 A | 8/1976 | Long, Jr. |
| 4,865,836 A | 9/1989 | Long, Jr. |
| 5,046,498 A | 9/1991 | Fishman |
| 5,271,401 A | 12/1993 | Fishman |
| 5,357,959 A | 10/1994 | Fishman |
| 5,383,858 A | 1/1995 | Reilly et al. |
| 5,505,932 A * | 4/1996 | Grinstaff ............... A61K 49/18 424/9.34 |
| 5,558,855 A | 9/1996 | Quay |
| 6,322,535 B1 | 11/2001 | Hitchins et al. |
| 6,652,489 B2 | 11/2003 | Trocki et al. |
| 6,773,673 B1 | 8/2004 | Layfield et al. |
| 7,553,294 B2 | 6/2009 | Lazzaro et al. |
| 7,666,169 B2 | 2/2010 | Cowan et al. |
| 9,173,955 B2 | 11/2015 | Ryall |
| 9,199,033 B1 | 12/2015 | Cowan et al. |
| 2002/0094317 A1 * | 7/2002 | Pines ................... G01R 33/282 424/9.3 |
| 2009/0297453 A1 | 12/2009 | Driehuys |
| 2013/0245604 A1 | 9/2013 | Kouyoumjian et al. |
| 2014/0027009 A1 | 1/2014 | Riley et al. |
| 2017/0035974 A1 | 2/2017 | Berry et al. |

FOREIGN PATENT DOCUMENTS

| | | |
|---|---|---|
| EP | 0620447 A2 | 10/1994 |
| WO | 9011045 A1 | 10/1990 |
| WO | 9527438 A1 | 10/1995 |
| WO | 2007127958 A2 | 11/2007 |
| WO | 2012155035 A1 | 11/2012 |
| WO | 2014144651 A2 | 9/2014 |

OTHER PUBLICATIONS

Ratner et al., Mag. Res. Med., 1987, 5, p. 548-554. (Year: 1987).*
Ebner et al., Circ Cardiovasc Imaging, 2010, p. 202-210. (Year: 2010).*
Huang et al., Magnetic Resonance Imaging, 2004, 22, p. 645-652. (Year: 2004).*
Scholz et al., Magnetic Resonance Imaging, 2009, 27, p. 549-556. (Year: 2009).*
Keipert; Peter E. Phd., "Oxygent, a Perfluorochemical-Based Oxygen Therapeutic for Surgical Patients", Blood Substitutes, Chapter 28, 2006, 312.
McGoron A.J.; et al, "Perfluorocarbon Distribution to Liver, Lung and Spleen of Emulsions of Perfluorotributylamine (FTBA) in Pigs and Rats and Perfluorooctyl Bromide (Pfob) in Rats and Dogs by 19F NMR Spectroscopy", Artificial Cells, Blood Substitutes, and Biotechnology, 1994, vol. 22/Iss. 4, 1243-1250.
Woodford; Chris, "Aerosol Cans", 2013.

(Continued)

*Primary Examiner* — Michael G. Hartley
*Assistant Examiner* — Leah H Schlientz
(74) *Attorney, Agent, or Firm* — Joseph L. Kent; David Schramm; James R. Stevenson

(57) ABSTRACT

A diagnostic contrast composition includes a carrier fluid and a non-decaying gas-evolving fluid incorporated in the carrier fluid. The gas-evolving fluid has a vapor pressure sufficient to evolve the gas from a circulatory system within a lung of a patient. The gas-evolving fluid is a composition containing a sufficient quantity of atoms with an atomic number higher than 8 to provide an increased absorption sufficient to increase a Hounsfield Unit measurement in an image in a CT imaging system. The gas-evolving fluid is selected from the group consisting of xenon gas, krypton gas, sulfur hexafluoride, a perfluorocarbon, a brominated perfluorocarbon, and combinations thereof. The carrier fluid is selected from the group consisting of water, saline, saline comprising one or more blood proteins, and saline comprising dissolved lipids.

13 Claims, 1 Drawing Sheet

(56) References Cited

OTHER PUBLICATIONS

"Extended European Search Report from EP Appln No. EP17206333", dated Sep. 17, 2018.
"Fluorocarbon-based injectable gaseous microbubbles for diagnosis and therapy", Current Opinion in Colloid and Interface Science, 2003, vol. 8, pp. 259-266.
"International Preliminary Report on Patentability from PCT Application No. PCT/US2016/018707", dated Aug. 31, 2017.
"International Search Report and Written Opinion from PCT Application No. PCT/US2016/018707", dated Apr. 29, 2016.
Kawabata Ken-Ichi; et al, "Nanoparticles with Multiple Perfluorocarbons for Controllable Ultrasonically Induced Phase Shifting", Japanese Journal of Applied Physics, Jun. 24, 2005, vol. 44/No. 6B, 4548-4552.
Kong Xiang; et al, "Xenon-Enhanced Dual-Energy CT Lung Ventilation Imaging: Techniques and Clinical Applications", AJR, 2014, 202, 309-317.
Mattrey; Robert F., "Perfluorooctylbromide: A New Contrast Agent for CT, Sonography, and MR Imaging", AJR, Feb. 1989, vol. 152, 247-252.
Riess; Jean G., "Reassessment of Criteria for the Selection of Perfluorochemicals for Second-Generation Blood Substitutes: Analysis of Structure/Property Relationships", Artificial Organs, Raven Press, New York, 1984, 8(1), 44-56.
Riess Jean G.; et al, "Solubility and Transport Phenomena in Perfluorochemicals Relevant to Blood Substitution and Other Biomedical Applications", J Nucl Med, Pergamon Press Ltd., 1982, vol. 54, No. 12, 2383-2406.
Ruiz-Cabello Jesus; et al, "Fluorine (19F) MRS and MRI in biomedicine", NMR Biomed, 2011, 24, 114-129.
Vidal Melo Marcos F.; et al, "Quantification of Regional Ventilation—Perfusion Ratios with PET", J Nucl Med, Dec. 2003, 44, 1982-1991.
Wallace; et al, "Multi-exponential Analysis of CPMG T2 Decay Curves for 129Xe Dissolved in Perfluoro-octyl Bromide Emulsions: Implications for Hyperpolarized Xenon Contrast Agent Development", Proc. Intl. Soc. Mag. Reson. Med., 2003, 11, 1378.

* cited by examiner

CONTRAST IMAGING AGENT WITH DISSOLVED GAS-EVOLVING FLUID

CROSS-REFERENCE TO RELATED APPLICATIONS

This application is Divisional of U.S. application Ser. No. 15/551,469, filed Aug. 16, 2017, which is a U.S. national stage filing under 35 U.S.C. § 371 of International Application No. PCT/US2016/018707, filed Feb. 19, 2016, which claims priority to U.S. Provisional Application No. 62/118,946, filed on Feb. 20, 2015 and titled "Contrast Imaging Agent With Dissolved Gas", and U.S. Provisional Application No. 62/118,517, filed on Feb. 20, 2015 and titled "A System and Method for Combined Gaseous/Liquid Imaging Agent Imaging", the disclosures of which are incorporated herein by reference in their entirety.

BACKGROUND OF THE DISCLOSURE

Field of the Disclosure

The present disclosure relates generally to a contrast agent for use in diagnostic imaging and to a method of using the contrast agent in a diagnostic imaging procedure, and more specifically, to a contrast agent having a gas-evolving fluid with augmented solubility and a method of using the contrast agent in a diagnostic imaging procedure.

Description of Related Art

There is often a medical need to assess one or more of the ventilation, air trapping, physical structure, gas exchange, and the perfusion status or capacity of the lungs or segments thereof in a patient, for example in the case of pulmonary embolism, COPD (Chronic Obstructive Pulmonary Disease), or IPF (Idiopathic Pulmonary Fibrosis). In practice, this assessment may be done using nuclear medicine imaging technology, X-ray-based imaging technology, or magnetic resonance (MR) imaging technology. Lung assessment using nuclear medicine imaging technology may include Single Photon Emission Computed Tomography (SPECT) with an inhaled SPECT agent and/or with a blood pool SPECT agent. Lung assessment using X-ray imaging technology may include Computed Tomography (CT) imaging of the patient's lungs while the patient is breathing xenon gas. The inhaled xenon gas may be imaged using CT as it dissolves in the patient's blood at the alveoli of the lung, for example to perform a perfusion study of an organ or region of the body. Lung ventilation may be also assessed with MR imaging by having the patient breathe F-19 containing gases or hyperpolarized xenon gas. Lung perfusion may also be assessed using, for example, a gadolinium based intravenously injectable contrast agent.

While the existing imaging modalities have a number of advantages for assessment of various lung characteristics, including function, condition, and disease state, they are also associated with a number of disadvantages. A typical dose of a SPECT imaging agent, such as 50 mCi of rubidium-82 (2E+11 atoms) or 10 mCi of flourine-18 (3.5E+12 atoms), allows collecting dynamic information without additional radiation exposure to the patient. While techniques based on nuclear medicine, including PET and SPECT, have high sensitivity and a single-dose radiation exposure, a drawback of these techniques is limited spatial resolution and relatively high image noise. A typical CT contrast dose of 100 ml of 370 mg of iodine per milliliter contrast corresponds to a dose of 6E+22 molecules and has the benefit of spatial resolution that is much higher than PET, with the temporal resolution being fractions of seconds. However, a drawback of CT technology is that an additional radiation dose is required for each image taken. With MR imaging, MR gadolinium contrast dosage is typically 10 ml of 1 mMol/ml (about 6E+21 atoms of gadolinium). MR has the ability to image hyperpolarized atoms, with a sensitivity several orders of magnitude greater. For example, volumes on the order of milliliters of gas are needed for an imaging procedure using hyperpolarized xenon. But, like cyclotron produced radioactivity, hyperpolarization decays spontaneously and requires special and expensive equipment for its creation. While MR generally has spatial and temporal resolution between that of CT and nuclear medicine with no radiation dose to the patient, the gadolinium contrast is not readily transferred to the air and the MR receives no signal from air in the lungs as there are almost no hydrogen atoms to image relative to the hydrogen atom content of the surrounding tissue.

All three modalities make use of inhaled contrast for lung studies. However, inhalation studies are complicated, involve complex, expensive, seldom used machines, and are thus not used in common clinical practice. Even for pulmonary embolism, where the mainstay was once ventilation/perfusion (VQ) SPECT, CT angiography with intravenous injections of iodinated contrast media is now becoming the preferred modality.

Methods described in U.S. Pat. No. 6,773,673 and International Application PCT/US2015/024203, the disclosures of which are incorporated herein, dissolve radioactive N-13 containing nitrogen gas, inject it intravenously, and then image the contrast in the vessels and the lungs with PET, PET/CT, or PET/MR. The N-13 isotope has a very short half-life, on the order of 10 minutes. A benefit of the short half-life is that the total radiation dose to which the patient is exposed is reduced. A similar study can be achieved in SPECT by dissolving a small amount of radioactive Xe-133 into saline and injecting it into the patient. Because of the sensitivity of PET and SPECT, sufficient radioactive N-13 or Xe-133 containing gas for the imaging procedure may be dissolved in saline at normal temperatures and pressures. Because of the sensitivity of PET and SPECT, sufficient N-13 containing gas for the imaging procedure may be dissolved in saline at normal temperatures and pressures. On the other hand, in addition to exposure to radiation for the patient and hospital personnel, an additional disadvantage of its short half-life is that the radioactive isotope must be generated near the imaging site, for example using relatively expensive, large and heavy cyclotrons. In addition, there is significant motion of the lungs during normal respiration, which cause significant blurring in a PET image. The present disclosure describes an alternate imaging process utilizing CT imaging of evolved gas that avoids the disadvantages associated with the current art, while addressing usability issues described herein. Thus, it would be desirable to have an injectable contrast imaging agent for CT that, upon reaching the lungs, evolves a CT-active gas into the airways of the lungs sufficient for diagnosis via CT.

SUMMARY OF DISCLOSURE

In view of the disadvantages of the existing imaging techniques in assessing lung function, condition, and disease state, there is a need in the art for an improved contrast imaging agent and method of imaging the lung using the improved contrast imaging agent that overcomes the deficiencies of the prior art. There is an additional need in the art for an injectable contrast imaging agent for CT that, upon reaching the lungs, evolves gas into the airways of the lungs sufficient for diagnosis via CT. In other aspects, there is a need in the art for a stable, injectable contrast agent for MR, that upon reaching the lungs, evolves gas into the airways of the lungs sufficient for diagnosis via MR.

In accordance with some aspects, a diagnostic contrast composition may include a carrier fluid and a non-decaying gas-evolving fluid incorporated in the carrier fluid. The gas-evolving fluid may have a vapor pressure sufficient to evolve the gas from a circulatory system within a lung of a patient. The gas-evolving fluid may be a composition containing a sufficient quantity of atoms with an atomic number higher than 8 to provide an increased absorption sufficient to increase a Hounsfield Unit measurement in an image in a CT imaging system. The gas-evolving fluid may be selected from the group consisting of xenon gas, krypton gas, and combinations thereof. The gas-evolving fluid may be selected from the group consisting of sulfur hexafluoride, a perfluorocarbon, a brominated perfluorocarbon, and combinations thereof. The carrier fluid may be selected from the group consisting of water, saline, saline comprising one or more blood proteins, and saline comprising dissolved lipids. The diagnostic contrast further may include at least one liquid or dissolved X-ray contrast imaging agent. A concentration of the gas-evolving fluid may be augmented by an increased pressure of the diagnostic contrast composition within a container or a delivery system. The pressure may be 1.5 atm to 30 atm. At least one concentration-augmenting composition may be dissolved in, suspended in, or emulsified in the carrier fluid to augment a concentration of the gas-evolving fluid. The concentration-augmenting composition may be a second gas-evolving fluid. The gas-evolving fluid may be a liquid or solid dissolved in, suspended in, or emulsified in the carrier fluid. In aspects where the contrast composition is used in MR imaging, the gas-evolving fluid may contain F-19 gas.

In accordance with other aspects, a method for making a diagnostic contrast composition may include providing a carrier fluid in a pressurizable container and dissolving a non-decaying gas-evolving fluid in a carrier fluid, wherein the gas-evolving fluid has a vapor pressure sufficient to evolve the gas from a circulatory system within a lung of a patient. The method may include augmenting a concentration of the gas-evolving fluid by dissolving the gas-evolving fluid in the carrier fluid at a pressure 1.5 atm to 30 atm. The gas-evolving fluid may be a composition containing a sufficient quantity of atoms with an atomic number higher than 8 to provide a Hounsfield Unit measurement to affect an image in a CT imaging system. The gas-evolving fluid may be selected from the group consisting of xenon gas, krypton gas, or combinations thereof. The gas-evolving fluid may be selected from the group consisting of sulfur hexafluoride, a perfluorocarbon, a brominated perfluorocarbon, and combinations thereof. The carrier fluid may be selected from the group consisting of water, saline, saline comprising one or more blood proteins, and saline comprising dissolved lipids.

In accordance with other aspects, a container including a diagnostic contrast composition may include a hollow container body with a pressurized interior space and the diagnostic contrast composition filling at least a portion of the pressurized interior space. The diagnostic contrast composition may include a carrier fluid and a gas-evolving fluid in the carrier fluid. The gas-evolving fluid may have a vapor pressure sufficient to evolve the gas from a circulatory system within a lung of a patient and a concentration of the gas-evolving fluid within the carrier fluid is augmented by an increased pressure within the pressurized interior space. The pressure in the pressurized interior space may be between 1.5 atm and 30 atm. The pressure within the pressurized interior space may be sustained during delivery of the diagnostic contrast composition from the pressurized interior space. The hollow container body may be a syringe having an open proximal end, an open distal end, and a circumferential sidewall extending between the proximal end and the distal end along a longitudinal axis. The proximal end may slidably receive a plunger to seal the proximal end, and a valve may seal the distal end. The valve may be a high-crack pressure valve that maintains the increased pressure of the pressurized interior space of the container body at a minimum pressure of 1.5 atm.

In accordance with further aspects, a method for imaging a lung of a patient may include
injecting a diagnostic contrast composition comprising a carrier fluid and a CT-active amount of a non-decaying gas-evolving fluid into a circulatory system of the patient wherein the gas-evolving fluid has a vapor pressure sufficient to evolve the gas from a circulatory system within a lung of a patient, and imaging the lung using a CT medical imager to produce at least a first image of the lung. Imaging the lung may be performed during at least one of: an inhalation period, a breath-hold period, and an exhalation period. Imaging the lung may be performed after a predetermined delay period after injection of the diagnostic contrast composition to allow the gas-evolving fluid to be delivered to the lungs by the circulatory system of the patient. The method may include imaging the lung to produce at least a second image of the lung after a predetermined delay period after injection of the diagnostic contrast composition. The at least the second image may be collected during at least one of an inhalation period, a breath-hold period, and an exhalation period. The gas-evolving fluid may be selected from the group consisting of xenon gas, krypton gas, sulfur hexafluoride, a perfluorocarbon, a brominated perfluorocarbon and combinations thereof.

Various aspects of the present disclosure may be further characterized by one or more of the following clauses:

Clause 1. A diagnostic contrast composition comprising: a carrier fluid, and a non-decaying gas-evolving fluid incorporated in the carrier fluid, wherein the gas-evolving fluid has a vapor pressure sufficient to evolve the gas from a circulatory system within a lung of a patient.

Clause 2. The diagnostic contrast composition of clause 1, wherein the gas-evolving fluid is a composition containing a sufficient quantity of atoms with an atomic number higher than 8 to provide an increased absorption sufficient to increase a Hounsfield Unit measurement in an image in a CT imaging system.

Clause 3. The diagnostic contrast composition of clause 1 or 2, wherein the gas-evolving fluid is selected from the group consisting of xenon gas, krypton gas, and combinations thereof.

Clause 4. The diagnostic contrast composition of any of clauses 1-3, wherein the gas-evolving fluid is selected from the group consisting of sulfur hexafluoride, a perfluorocarbon, a brominated perfluorocarbon, and combinations thereof.

Clause 5. The diagnostic contrast composition of any of clauses 1-4, wherein the carrier fluid is selected from the group consisting of water, saline, saline comprising one or more blood proteins, and saline comprising dissolved lipids.

Clause 6. The diagnostic contrast composition of any of clauses 1-5, wherein the diagnostic contrast further comprises at least one liquid or dissolved X-ray contrast imaging agent.

Clause 7. The diagnostic contrast composition of any of clauses 1-6, wherein a concentration of the gas-evolving fluid is augmented by an increased pressure of the diagnostic contrast composition within a container or a delivery system.

Clause 8. The diagnostic contrast composition of clause 7, wherein the pressure is 1.5 atm to 30 atm.

Clause 9. The diagnostic contrast composition of any of clauses 1-8, further comprising at least one concentration-augmenting composition dissolved in, suspended in, or emulsified in the carrier fluid to augment a concentration of the gas-evolving fluid.

Clause 10. The diagnostic contrast composition of clause 9, wherein the concentration-augmenting composition is a second gas-evolving fluid.

Clause 11. A method for making a diagnostic contrast composition, the method comprising: providing a carrier fluid in a pressurizable container; and dissolving a non-decaying gas-evolving fluid in a carrier fluid, wherein the gas-evolving fluid has a vapor pressure sufficient to evolve the gas from a circulatory system within a lung of a patient.

Clause 12. The method of clause 11, further comprising augmenting a concentration of the gas-evolving fluid by dissolving the gas-evolving fluid in the carrier fluid at a pressure 1.5 atm to 30 atm.

Clause 13. The method of clause 11 or 12, wherein the gas-evolving fluid is a composition containing a sufficient quantity of atoms with an atomic number higher than 8 to provide a Hounsfield Unit measurement to affect an image in a CT imaging system.

Clause 14. The method of any of clauses 11-13, wherein the gas-evolving fluid is selected from the group consisting of xenon gas, krypton gas, or combinations thereof.

Clause 15. The method of any of clauses 11-13, wherein the gas-evolving fluid is selected from the group consisting of sulfur hexafluoride, a perfluorocarbon, a brominated perfluorocarbon, and combinations thereof.

Clause 16. The method of any of clauses 11-15, wherein the carrier fluid is selected from the group consisting of water, saline, saline comprising one or more blood proteins, and saline comprising dissolved lipids.

Clause 17. A container including a diagnostic contrast composition, the container comprising: a hollow container body with a pressurized interior space; and the diagnostic contrast composition filling at least a portion of the pressurized interior space, the diagnostic contrast composition comprising: a carrier fluid, and a gas-evolving fluid in the carrier fluid, wherein the gas-evolving fluid has a vapor pressure sufficient to evolve the gas from a circulatory system within a lung of a patient and a concentration of the gas-evolving fluid within the carrier fluid is augmented by an increased pressure within the pressurized interior space.

Clause 18. The container of clause 17, wherein the pressure in the pressurized interior space is between 1.5 atm and 30 atm.

Clause 19. The container of clause 17 or 18, wherein the pressure within the pressurized interior space is sustained during delivery of the diagnostic contrast composition from the pressurized interior space.

Clause 20. The container of any of clauses 17-19, wherein the hollow container body is a syringe having an open proximal end, an open distal end, and a circumferential sidewall extending between the proximal end and the distal end along a longitudinal axis, wherein the proximal end slidably receives a plunger to seal the proximal end, and wherein a valve seals the distal end.

Clause 21. The container of clause 20, wherein the valve is a high-crack pressure valve that maintains the increased pressure of the pressurized interior space of the container body at a minimum pressure of 1.5 atm.

Clause 22. A method for imaging a lung of a patient, the method comprising: injecting a diagnostic contrast composition comprising a carrier fluid and a CT-active amount of a non-decaying gas-evolving fluid into a circulatory system of the patient wherein the gas-evolving fluid has a vapor pressure sufficient to evolve the gas from a circulatory system within a lung of a patient; and imaging the lung using a CT medical imager to produce at least a first image of the lung, wherein imaging the lung is performed during at least one of: an inhalation period, a breath-hold period, and an exhalation period.

Clause 23. The method of clause 22, wherein imaging the lung is performed after a predetermined delay period after injection of the diagnostic contrast composition to allow the gas-evolving fluid to be delivered to the lungs by the circulatory system of the patient.

Clause 24. The method of clause 22 or 23, further comprising imaging the lung to produce at least a second image of the lung after a predetermined delay period after injection of the diagnostic contrast composition,
wherein the at least the second image is collected during at least one of an inhalation period, a breath-hold period, and an exhalation period.

Clause 25. The method of any of clauses 22-24, wherein the gas-evolving fluid is selected from the group consisting of xenon gas, krypton gas, sulfur hexafluoride, a perfluorocarbon, a brominated perfluorocarbon and combinations thereof.

These and other features and characteristics of the contrast imaging agent, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only. As used in the specification and the claims, the singular form of "a", "an", and "the" include plural referents unless the context clearly dictates otherwise.

DETAILED DESCRIPTION

Figure 1:
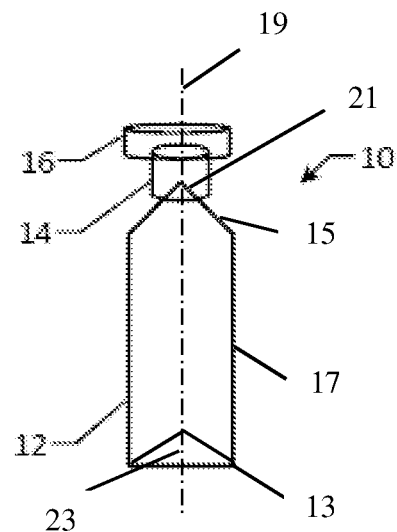
FIG. 1 is a side view of a container for storing a diagnostic contrast composition according to an aspect of the present disclosure.

For purposes of the description hereinafter, the terms "upper", "lower", "right", "left", "vertical", "horizontal", "top", "bottom", "lateral", "longitudinal", and derivatives thereof shall relate to the components as they are oriented in the drawing figures. When used in relation to a syringe, the term "proximal" refers to a portion of a syringe nearest a fluid injector when a syringe is oriented for connecting to a fluid injector. The term "distal" refers to a portion of a syringe farthest away from a fluid injector when a syringe and/or a plunger is oriented for connecting to a fluid injector. The term "circumferential" refers to a direction around an inner or outer surface of a sidewall of a syringe. The term "axial" refers to a direction along a longitudinal axis of a syringe extending between the proximal and distal ends. The term "CT-active amount" refers to an amount of an X-ray contrast agent sufficient to get visualization of an X-ray contrast on a CT medical imager. The term "MR-active amount" refers to an amount of an MR contrast agent sufficient to get visualization on an MR medical imager. The term "augmented solubility" refers to an increased concentration of a gas-evolving fluid over its solubility at standard temperature and pressure. The term "airspace" refers to passages and gaseous space of the alveoli, the bronchiole, bronchi, trachea, and all other air containing structures of the lung. The term "non-decaying" refers to materials whose imaging related properties do not decay over time. Examples of decaying image properties are radioactivity and hyperpolarization which decay over time. It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting.

Referring to the drawings in which like reference characters refer to like parts throughout the several views thereof, the present disclosure is generally directed to an injectable diagnostic contrast composition (also referred to herein as "contrast agent") for CT or MR that, upon reaching the lungs of a patient, evolves gas into the airspace of the lungs sufficient for diagnosis via CT or MR imager. The present disclosure is further directed to a method of making the diagnostic contrast composition, and a method of imaging the lungs of a patient using the diagnostic contrast composition. Various aspects of the present disclosure are related to a container for the diagnostic contrast composition.

In various aspects, the injectable diagnostic contrast composition contains a gas-evolving fluid that is incorporated in a carrier fluid, such as by dissolution in the carrier fluid. As used herein, "gas-evolving fluid" includes a solution or suspension having at least one gaseous, liquid, or solid compound dissolved, suspended, or emulsified therein, wherein the at least one compound is CT-active and has a vapor pressure that is high enough to be released as a gas across the membrane of the alveoli of the lungs during respiration, when transported to the alveoli by the circulatory system of the patient to which the injectable diagnostic contrast composition has been administered. In specific aspects, the gas-evolving fluid is in at least sufficient concentration in the contrast composition to release sufficient CT-active gas to be imaged by a CT imager. In various aspects the gas-evolving fluid may be non-decaying. Once injected into patient's bloodstream, the gas-evolving fluid evolves from the carrier fluid such that the gas-evolving fluid may be useful in CT or MR imaging. The gas-evolving fluid is desirably selected to have a vapor pressure sufficient to evolve the gas from a circulatory system within a lung of a patient. The gas-evolving fluid is desirably selected to be non-toxic and non-allergenic. In some aspects, the gas-evolving fluid is a composition containing a sufficient quantity of atoms with an atomic number higher than 8 to provide an increased absorption sufficient to increase a Hounsfield Unit measurement in an image in a CT imaging system. The diagnostic contrast composition may be packaged such that it is ready for injection into the body or vasculature of the patient.

In various aspects, the gas-evolving fluid may be a non-decaying gas or liquid that has a vapor pressure sufficient to evolve the gas from a circulatory system within a lung of a patient. For CT imaging, the gas-evolving fluid desirably has sufficient X-ray absorbance characteristics to that of commonly used X-ray contrast. For MR imaging, the gas-evolving fluid may be F-19 gas that has a vapor pressure sufficient to evolve the F-19 gas from a circulatory system within a lung of a patient.

An example of a high concentration iodine X-ray contrast is ULTRAVIST® 370, which contains 370 mg of iodine per mL of liquid. Lower concentrations of iodine contrast agents are available, too. In one exemplary and non-limiting aspect, the noble gas xenon may be selected as the gas-evolving fluid that may be dissolved in a liquid for injection into a patient. In other aspects, the gas-evolving fluid may be a composition containing a sufficient quantity of atoms with an atomic number higher than 8 to provide a Hounsfield Unit measurement to measurably affect an image in a CT imaging system. For example utilizing conventional CT imagers, a change on the order of 10 HU or 5 HU is measurable. As scanning technologies advance, the measurable change in Hounsfield Units may decrease. For example, xenon breathed in for cerebral blood flow measurements results in an increase in 10 Hounsfield units (HU) which is reliably detectable by CT imagers. In other exemplary and non-limiting aspects, the gas-evolving fluid may be krypton gas or a combination of krypton and xenon gases. In further exemplary and non-limiting aspects, the gas-evolving fluid may be sulfur hexafluoride, a perfluorocarbon, a brominated perfluorocarbon, and combinations thereof. As used herein, "perfluorocarbon" means a C1-C12 cyclic, linear, or branched saturated or unsaturated alkane, alkene, or aryl compound in which at least 90% of the hydrogen atoms have been replaced by fluorine atoms. As used herein, "brominated perfluorocarbon" means a perfluorocarbon having at least one bromine atom. The gas-evolving fluid may be a gas, liquid, or solid dissolved in, suspended in, or emulsified in the carrier fluid. The gas-evolving fluid may be a gas, liquid, or solid dissolved in, suspended in, or emulsified in the carrier fluid. In some aspects, the gas-evolving fluid may be a high-volume fraction of microbubbles formed as a foam.

As discussed herein, the gas-evolving fluid is incorporated in a carrier fluid. In various aspects, the carrier fluid may be an injectable liquid that is biocompatible with the patient's circulatory system. In various exemplary and non-limiting aspects, the carrier fluid may be water, saline, saline comprising one or more blood proteins, and saline comprising dissolved lipids. Alternatively, in certain aspects where the gas-evolving fluid is a liquid, for example, but not limited to perfluorocarbons and brominated perfluorocarbons, the liquid may also serve as the carrier fluid and be injected directly into the patient.

Xenon gas is an inert gas and has an atomic number (54) that is similar to that of iodine (53), such that its X-ray absorbance characteristics are very similar to that of iodine. Xenon gas has a relatively high solubility in water or aqueous solutions, and a significantly higher solubility in oil.

Relevant properties of xenon gas at body temperature (37° C.) are listed in Table 1 below.

TABLE 1

| | xenon | |
|---|---|---|
| temp | 37 | C. |
| atomic number | 54 | |
| molar weight | 131 | gm |
| gas volume STP | 22.4 | liter |
| density | 0.005848 | gm/ml |
| | 5.848214 | mgm/ml |
| bunsen constant | 0.085 | water |
| bunsen constant | 0.1105 | seawater (*1.3 of pure water) |
| bunsen constant | 1.7 | olive oil 20 ratio al |
| Ostwald solubility coeff. | 0.13 | blood |

*British Journal of Anaesthesia* 1998; 80: 255-256

Dissolution of xenon gas in liquid, such as saline or other medical fluid, including an iodine X-ray contrast solution, provides a diagnostic contrast composition with a variety of available concentrations of xenon (mg) per mL of liquid based on a number of parameters, including pressure or presence of one or more concentration-augmenting compositions. For example, the concentration of the gas-evolving fluid in the carrier fluid may be dependent on pressure and temperature. In certain circumstances, it may be desirable to augment the concentration of the gas-evolving fluid beyond the carrying capacity of the carrier fluid at, for example, standard temperature and pressure. For example, according to Henry's Law, the amount of a gas dissolved in a liquid is proportional to the partial pressure of the gas in the volume of the liquid at a given temperature. Table 2 below uses the coefficients from Table 1 above to compute the amount of xenon gas that is dissolved in water, blood, and oil based on increasing pressure (from 1 atm to 30 atm).

TABLE 2

| | Amount of Gas Dissolved in the Liquid | | | | | |
|---|---|---|---|---|---|---|
| Pressure | 1 | 2 | 4 | 5 | 30 | atm |
| saline | 0.497098 | 0.994196 | 1.988393 | 2.485491 | 14.91295 | mgmXe/ml |
| blood | 0.760268 | 1.520536 | 3.041071 | 3.801339 | 22.80804 | mgmXe/ml |
| oil | 9.941964 | 19.88393 | 39.76786 | 49.70982 | 298.2589 | mgmXe/ml |

From Table 2 above, a pressure on the order of 30 atm (atmospheres) results in enough xenon gas incorporated in oil to approach the concentration of the more highly concentrated iodine-based contrasts, such as ULTRAVIST® 370 discussed above. In this manner, the concentration of the gas-evolving liquid (xenon) in a carrier fluid (saline, blood, oil, etc.) may be augmented by controlling the pressure of the gas-evolving liquid. Similarly, the concentration of F-19 gas in a carrier fluid may be augmented by controlling the pressure of the F-19 gas when used for MR imaging.

In order to visualize the contrast composition on a CT medical imager, the contrast composition must have sufficient contrast against the surrounding tissue in order to attenuate the X-ray beam from the CT medical imager. For CT imaging, attenuation is measured in Hounsfield Units (HU) which define radiodensity of a material at standard temperature and pressure. The image contrast that results depends upon the voltage (in kVp) of the X-ray tube. The attenuation per mg I/mL of ULTRAVIST® 370 dissolved in blood is about 19 HU/mgL/ml at 140 kVp and 32 HU/mg I/mL at 90 kVp. For a contrast composition having xenon gas as the gas-evolving fluid, a pressure of 2 atm will achieve a xenon concentration in an oily solvent that will produce about 600 HU of image contrast at 90 kVp. When injected and diluted 10:1 by blood on its way to the right half of the heart, this composition produces about 60 HU of image contrast, which can be readily seen on a CT image. In some aspects, 80 HU of image contrast may be produced at 40% xenon content. 10-20 HU may be sufficient to produce an image of desired quality.

To obtain higher levels of opacification of the lung tissue and/or airways, it may be desirable to incorporate additional gas-evolving fluid, that is, to augment the concentration of the gas-evolving fluid in the carrier fluid. An additional way to augment the amount of gas-evolving fluid that may be associated with a given total volume of carrier fluid is to incorporate a secondary fluid or compound into the carrier fluid, either through dissolution, suspension, or emulsification, where the secondary fluid or compound increases the carrying capacity of the carrier fluid to dissolve, suspend, or emulsify higher concentrations of the gas-evolving fluid. Example secondary fluids include perfluorocarbons or brominated perfluorocarbons. A particular non-limiting example is Perflubron [perfluorooctylbromide (PFOB)], which is commercially available as a 30% emulsion in saline. PFOB has been used as a blood substitute, OXYGENT™ and is manufactured by Alliance Pharmaceutical Corp., San Diego, Calif.

Table 3 below illustrates an exemplary embodiment of a contrast composition where both pressurization and a secondary fluid are used to augment the solubility of the gas-evolving fluid in a carrier fluid. Given a lung volume of about 6 liters and a targeted xenon gas concentration in the airway to be imaged of 10%, the amount of xenon gas that is needed is equivalent to about 3.5 grams of xenon.

TABLE 3

| Lung Volume | 6 liters |
|---|---|
| | 10% Xenon target |
| | 0.026786 moles xenon |
| | 131 molecular weight gm/M |
| | 3.508929 gm xenon needed |

Table 4 lists the volume of the contrast composition required to deliver the 3.5 g of xenon gas at various pressures and carrier fluid compositions. Common CT injections are under 200 ml and often preferably under 150 ml. Thus, in an exemplary aspect where xenon gas is incorporated into a carrier fluid at a pressure of 5 atmospheres (75 psi) and a 50% emulsion, a total volume of the contrast composition that needs to be injected into the patient for imaging is about 141 ml or more. By increasing the pressure to 10 atm (147 psi), with a 30% emulsion, the total injection volume is 118 ml. At 10 atm and a 50% emulsion, the total injection volume is 71 ml. By this manner, various concentrations and pressures of the contrast composition may be prepared to provide sufficient evolved gas within the lung for accurate imaging using CT.

TABLE 4

Volume of fluid to inject (ml)

| Pressure | 1 | 2 | 4 | 5 | 10 | 30 | atm |
|---|---|---|---|---|---|---|---|
| saline | 7059 | 3529 | 1765 | 1412 | 706 | 235 | |
| blood | 4615 | 2308 | 1154 | 923 | 462 | 154 | |
| oil | 353 | 176 | 88 | 71 | 35 | 12 | |
| 30% emulsion | 1176 | 588 | 294 | 235 | 118 | 39 | |
| 50% emulsion | 706 | 353 | 176 | 141 | 71 | 24 | |

In various alternative aspects, a secondary fluid being used to augment the carrying ability of the carrier fluid for the gas-evolving fluid may be selected from one of the perfluorocarbons mentioned in Perfluorooctylbromide: A New Contrast Agent for CT, Sonography, and MR Imaging by Robert F. Mattrey, AJR 152:247-252, February 1989 0361-803X/89/1 522-0247. The perfluorocarbon additionally may serve as a gas-evolving fluid which augments the opacification or X-ray absorption of the airspace of the lungs. Bromine, while not as absorbent as xenon gas is significantly more absorbent than air. In addition, by having the enhanced carrying capacity fluid moving into the airspace, more of the gas-evolving fluid also crosses into the airspace.

Much previous work on perfluorocarbons as gas carrying fluids or concentration-augmenting fluids has focused on blood replacement. Perfluorocarbons are desirable because they can dissolve 20 or more times the amount of oxygen than water. These molecules are generally inert and not metabolized in an organism, even in large quantities, similar to current X-ray and MRI contrast molecules. For use as blood replacements, several factors need to be considered. The first is that large quantities, on the order of liters, are needed. The second is that the molecules chosen for blood replacement need to have sufficiently slow elimination or exhalation to have a sufficiently long retention in the body for the treatment to be sufficient. In the research for blood replacements, it was found that lower molecular weight perfluorocarbons caused emphysema, presumably due to their high vapor pressures and thus rapid exhalation. Thus, lower molecular weight perfluorocarbons, used at concentrations below those shown to cause emphysema, may be useful as gas-evolving fluids described herein.

In certain embodiments of this disclosure, relatively rapid gas evolution into the airways of the lung for imaging may be desired. Thus for either a gas-evolving fluid and/or a gas concentration-augmenting fluid, it may be desirable to have more rapid exhalation, evaporation, and/or transportation of the fluid into the lungs than is commonly desirable for a blood replacement fluid. In addition, because only grams of evolved gas are needed in the lung airspaces for CT imaging, the volume or concentration of the perfluorocarbon fluid that needs to be injected as a diagnostic contrast may be considerably less than in the case of blood replacement.

The following references are listed and incorporated herein by reference to illustrate some of the state of the art around perfluorocarbons as concentration augmentation fluids, gas transport fluids, and gas-evolving fluids, as well as CT and MR imaging:

Perfluorooctylbromide: A New Contrast Agent for CT, Sonography, and MR Imaging by Robert F. Mattrey, AJR 152:247-252, February 1989, 0361-803X/89/1 522-0247;

Quantification of Regional Ventilation—Perfusion Ratios with PET; Marcos F. Vidal Melo, MD, PhD; Dominick Layfield, MSc; R. Scott Harris, MD; Kevin O'Neill, MSc; Guido Musch, MD; Torsten Richter, MD; Tilo Winkler, PhD; Alan J. Fischman, MD, PhD; and Jose G. Venegas, PhD; J Nucl Med 2003; 44:1982-1991;

U.S. Pat. No. 6,773,673 Radiation handling system and set;

Solubility And Transport Phenomena In Perfluorochemicals Relevant To Blood Substitution And Other Biomedical Applications; Jean G. Riess and Maurice Le Blanc; Pure & Appl. Chem., Vol. 54, No. 12, pp. 2383-2406, 1982;

Reassessment of Criteria for the Selection of Perfluorochemicals for Second-Generation Blood Substitutes: Analysis of Structure/Property Relationships; Jean G. Riess; Artificial Organs, 8(1):44-56, Raven Press, New York, 1984 International Society for Artificial Organs;

U.S. Pat. No. 4,865,836 A, Brominated perfluorocarbon emulsions for internal animal use for contrast enhancement and oxygen transport, gives information about perfluorooctylbromide and similar perfluorocarbons;

Xenon-Enhanced Dual-Energy CT Lung Ventilation Imaging: Techniques and Clinical Applications; Xiang Kong, Hui Xue Sheng, Guang Ming Lu, Felix G. Meinel, Kevin T. Dyer, U. Joseph Schoepf, Long Jiang Zhang; AJR 2014; 202:309-317; DOI:10.2214/AJR.13.11191; and Fluorine (19F) MRS and MRI in biomedicine; Jesus Ruiz-Cabelloa, Brad P. Barnetta, Paul A. Bottomleya, and Jeff W. M. Bulte; NMR Biomed. 2011; 24: 114-129.

Perfluorocarbons, in the strictest sense, include only molecules containing carbon and fluorine, with fluorine taking the place of hydrogen in the normal organic or hydrocarbon molecule. Perfluorocarbons, in the broader sense, as it is being used in this patent, include molecules containing at least carbon and fluorine substituted for multiple of the normal hydrogen atoms and may include other atoms such as but not limited to bromine, chlorine, nitrogen, and oxygen.

Perfluorooctylbromide, as mentioned herein as both a concentration enhancing compound and a gas evolving compound, has a molecular weight of 498.96 gm and a boiling point of 142° C. This compound has a retention half-life (i.e., time required for an initial amount in the body to fall to half of its value) in rats of about 6 hours and a shorter retention half-life in humans. Most of the material is removed through the lungs. As the perfluoroalkyl bromides with shorter carbon chains are used, both the molecular weight and boiling point decrease, causing the half-life to shorten as well. Thus, by using concentrations of shorter chain perfluoroalkyl bromides, for example 1-bromoperfluorohexane, 1-bromononafluorobutane, or heptafluoro-n-propyl bromide, the ratio of the gas evolving from the gas evolving fluid dissolved in the concentration augmenting fluid decreases and more of the total gas volume evolved comes directly from the evaporation or gasification of the concentration augmenting fluid. In addition, the oxygen carrying capacity increases with decreased chain length. Mixtures of various gas evolution rates may be determined with reference to Table 5 below.

TABLE 5

| Molecule | Molecular Weight (gm) | Boiling Point (° C.) |
|---|---|---|
| Perfluorooctylbromide | 498.96 | 142 |
| 1-bromoperfluoroheptane | 448.95 | 118 |

TABLE 5-continued

| Molecule | Molecular Weight (gm) | Boiling Point (° C.) |
|---|---|---|
| 1-bromoperfluorohexane | 398.95 | 97 |
| 1-bromononafluorobutane | 298.93 | 43-44 |
| Heptafluoro-N_propyl bromide | 248.92 | 12 |

In general, the solubilities of gases in perfluorocarbons are higher than in water by a factor of 20 or more if expressed in vol. %, or of 200 if expressed in molar fractions, but are only a factor of less than 3 above those in related hydrocarbons. For MR imaging, the increased atomic number of the bromine atom is not important and thus molecules with only fluorine and carbon may be used advantageously for F-19 imaging. Table 6 below indicates the boiling point and vapor pressure for various simple perfluorocarbons. For MR imaging, an example diagnostic contrast may contain an emulsion of a mixture with a significant portion of Perfluoropentane, perfluoro-isobutane, Perfluorobutane, or Perfluoropropane as the gas evolving fluid and some amount of Perfluorooctylbromide, 1-bromoperfluoroheptane, or 1-bromoperfluorohexane as the concentration enhancing fluid.

TABLE 6

| Molecule | Molecular Weight (gm) | Boiling Point (° C.) | Vapor pressure at 15C |
|---|---|---|---|
| Perfluorohexane | 338 | 56 | 27 kPa @ 25C (.27 atm.) |
| Perfluoropentane | 288 | 28 | 84 kPa @ 25C (.82 atm.) |
| perfluoro-isobutane | 238 | 2.1 | |
| Perfluorobutane | 238 | −1.7 | 330 kPa @ 25C (3.2 atm.) |
| Perfluoropropane | 188 | −37 | |
| Hexafluoroethane | 138 | −78 | 3 MPa @ 15C (30 atm.) |
| Carbon tetraflouride | 88 | −128 | 3.7 MPa @ 15C (36 atm.) |

In an alternative aspect, the brominated perfluorocarbon emulsified in a carrier fluid, for example, saline at room temperature and pressure, may be the gas-evolving fluid sufficient for airspace opacification. In a further alternative aspect, the carrier fluid may also incorporate a non-gas-evolving X-ray absorbing material to opacify the vasculature and or the tissue of the lung. This can be of use in diagnosing some diseases or conditions such a vascular disease of various type, edema, and fibrosis or scaring. This X-ray absorbing material may be a solid dissolved in the carrier fluid, as is done with common iodinated X-ray contrast. In certain aspects, the non-gas-evolving material may be the long half-life brominated perfluorocarbon. In other aspects, the non-gas-evolving material may be small molecules that can diffuse from the vasculature into the intracellular space, or it may be a material that is generally constrained to the vascular volume.

The ability to have a tracer that flows into a region of interest through the arterial supply to a tissue and then out both through the venous path and via the airspace/airways makes it possible to do sophisticated dynamic analysis, for example first pass dye dilution type analyses and more sophisticated pharmacokinetic and compartmental analyses.

In aspects including a gaseous gas-evolving fluid, to maintain the concentration of gas-evolving fluid, such as xenon gas, incorporated in a liquid carrier fluid, it is preferable to store the liquid contrast composition in a pressurized state to prevent evolving of the xenon gas from the carrier fluid. A pressure of 2 atm or higher is sufficient to maintain the xenon gas at its augmented solubility in the carrier fluid. At the same time, the pressure of at least 2 atm may still be low enough to allow for cost effective packaging. Furthermore, the pressure of at least 2 atm may allow any xenon gas bubbles that come out of solution from the carrier of the contrast composition to readily dissolve in blood when the contrast composition is injected into the patient's bloodstream. Additionally, the pressure of at least 2 atm is low enough to transportation of a storage container using conventional shipping methods, including airplane transport. Because conventional CT injectors operate at pressures up to 300 psi, injecting a contrast composition which needs to have the injection pressure of at least 30 psi (about 2 atm) is well within the normal operating range of the CT injector.

With reference to FIG. 1, a container, for example syringe 10, for a contrast composition is shown in accordance with one exemplary and non-limiting aspect. The syringe 10 generally has a cylindrical hollow container body 12 formed from glass, metal, or a suitable medical-grade plastic. The syringe 10 may be a syringe for use with a CT injector. The body 12 has a proximal end 13 and a distal end 15, with a circumferential sidewall 17 extending therebetween along a longitudinal axis 19 extending through a center of the body 12. The body 12 may be made from a transparent or translucent material. A nozzle 21 extends from the distal end 15 of the body 12. The proximal end 13 of the body 12 may be sealed with a plunger 23 that is slidably and reciprocally movable through an interior space of the body 12. The plunger 23 may have a plunger cover (not shown) that forms a liquid-tight seal against an inner surface of the sidewall 17 as the plunger 23 is advanced therethrough.

With continued reference to FIG. 1, the syringe 10 may have a high-crack pressure valve 14 on the nozzle 21, and a gas tight cap 16 to prevent escape of gas or liquid from the interior of the syringe 10 through the high-crack pressure valve 14. In some aspects, the high-crack pressure valve may be the valve disclosed in WO 2014/0144651, the disclosure of which is incorporated herein in its entirety. The high-crack pressure valve 14 ensures that the contrast remains pressurized until the latest possible time before delivery to the patient, thus helping to reduce formation of gas bubbles and ensuring accurate dosing.

Figure 2:
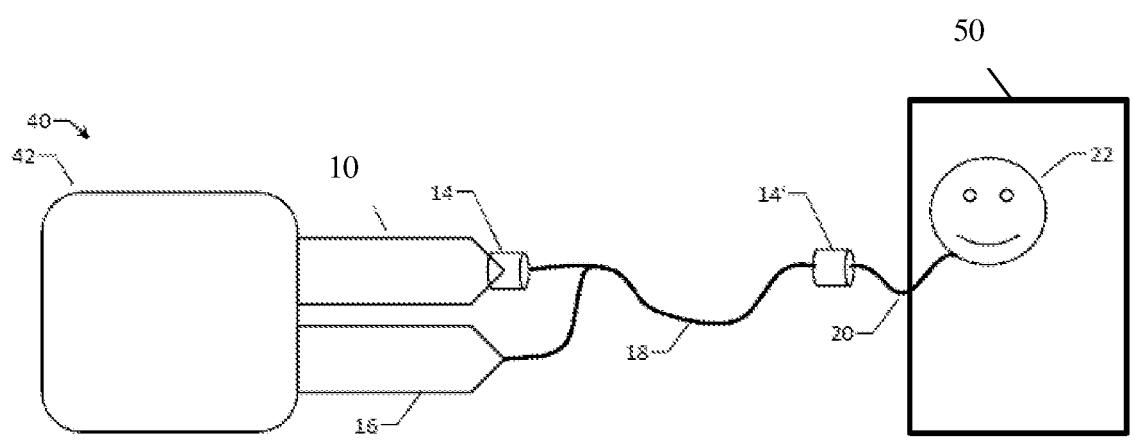
FIG. 2 is a schematic view of an injection and imaging system for injecting and imaging a diagnostic contrast composition according to another aspect of the present disclosure.

With continued reference to FIG. 1, the proximal end 13 of the syringe 10 is sized and adapted for being removably inserted in the port 25 of an injector 40 (shown in FIG. 2). Exemplary syringe 10 suitable for use with the injector 40 depicted in FIG. 2, is described in U.S. Pat. No. 5,383,858 to Reilly et al., which is assigned to the assignee of the present application, the disclosure of which is incorporated by reference in its entirety. Additional exemplary syringes are disclosed in, for example, U.S. Pat. No. 6,322,535 to Hitchins et al.; U.S. Pat. No. 6,652,489 to Trocki et al.; U.S. Pat. No. 9,173,955 to Tucker et al.; and U.S. Pat. No. 9,199,033 to Cowan et al.; all of which are assigned to the assignee of the present application, and the disclosures of which are incorporated by reference in their entireties.

In various aspects, the contrast composition is stored directly in the interior space of the syringe 10. Desirably, the contrast composition may be stored at an elevated pressure, such as about 2 atm, to prevent evolution of gas evolving fluid from the carrier fluid. Injection of the contrast composition may take place directly from the syringe 10. In an alternative aspect, the contrast composition may be stored in a container in which a proximal end is pushed towards a distal end such that a sidewall of the container rolls upon itself as a rolling diaphragm. Such a container is described in U.S. Provisional Application Nos. 61/984,386 and 61/987,086, the disclosures of which are incorporated herein by reference in their entirety.

With reference to FIG. 2, the contrast composition may be injected into the patient's bloodstream using a medical fluid delivery system 40 having a fluid injector 42, such as a CT injector. The injector 42 may be used during a medical procedure, such as a CT imaging procedure, to inject the contrast composition from the syringe 10 into the body of the patient 22 by driving the plunger 23 (shown in FIG. 1) of the syringe 10 with at least one piston. The injector 42 may be a multi-syringe injector, wherein several syringes 10 may be oriented in a side-by-side or other arrangement and include plungers 23 separately actuated by respective pistons associated with the injector 10. In some aspects, the fluid injector 42 may be configured to receive at least one syringe 10 filled with the contrast composition and one or more second syringes 16 filled with a different fluid from that of the syringe 10, such as saline or another contrast agent that may be used to fluid the contrast composition into the patient. The delivery of fluid from both syringes 10, 16 is controlled by the injector 42. Fluid flow from the at least one syringe 10 may be regulated by a fluid control module (not shown). The fluid control module may operate various pistons, valves, and/or flow regulating structures to regulate the delivery of the medical fluid, such as saline solution and contrast, to the patient based on user selected injection parameters, such as injection flow rate, duration, total injection volume, and/or ratio of contrast media and saline. One example of a suitable front-loading fluid injector 42 that may be modified for use with the above-described system including at least one syringe 10 is disclosed in U.S. Pat. No. 5,383,858 to Reilly et al.; U.S. Pat. No. 9,173,955 to Tucker et al.; and U.S. Pat. No. 9,199,033 to Cowan et al., all which are incorporated by reference in their entirety. Another example of relevant multi-fluid delivery systems that may be modified for use with the present system are found in U.S. Pat. No. 7,553,294 to Lazzaro et al.; U.S. Pat. No. 7,666,169 to Cowan et al.; International Patent Publication No. WO 2012/155035; and United States Patent Application Publication No. 2014/0027009 to Riley et al.; the disclosures of which are incorporated herein by reference.

A delivery line 18 may be connected to the output of the two syringes as shown. In certain aspects, the delivery line 18 may also incorporate a high-crack pressure valve 14' to be connected to the IV or other vascular access fluid path sets 20 connected to patient 22. Alternatively, the IV or other vascular access fluid path 20 could have a high-crack pressure valve anywhere along the length of the fluid path, optionally at the outlet of the IV in the patient's blood vessel. The fluid delivery system 40 is configured for use with a medical imaging system 50, such as a CT or an MR scanner. The combination of the delivery system 40 and the imaging system 50 may be used to assess one or more of the ventilation, air trapping, physical structure, gas exchange, and the perfusion status or capacity of the lungs or segments thereof in the patient 22.

Having described the contrast composition and storage of the same in accordance with various aspects of the present disclosure, a method of imaging a lung of a patient using a CT imager will now be described. A similar procedure may be used for imaging using an MR imager. Prior to scanning the patient 22, the delivery system 40 is prepared for injecting fluid into the patient 22. One or more syringes 12 containing a contrast composition, described herein in accordance with one or more aspects, is loaded onto the injector 42, assuring that the pressure within the one or more syringes 10 is maintained. In addition, one or more second syringes 16 may be loaded onto the injector 42 for flushing the contrast composition from the one or more syringes 10 once injected into the patient 22. A delivery line 18 is then connected to the one or more syringes 10, 16 for delivering fluid from the one or more syringes 10, 16 to the patient 22. The delivery system 40 may then be primed, after which the delivery system 40 is ready for injecting fluid into the patient 22.

Initially, the patient 22 is placed on a bed of the imaging system 50, usually lying flat on the back, side, or stomach. For some lung imaging, however, it may be desirable for the patient to be in the upright position. The imaging protocol may be as follows: starting with a contrast-free lung, a bolus having a CT-active amount of the contrast composition is injected into a vein of the patient 22 using the injector 42. Simultaneously, or after a predetermined delay (5 s to 15 s), the imaging system 50 collects one or more consecutive images while the patient 22 holds his/her breath. During this breath-hold phase, the gas from the gas-evolving fluid evolves from the circulatory system to be within the airspace of the lungs of the patient 22. At the end of the breath-hold phase, such as after 5 s to 15 s, the imaging system 50 may continue to collect one or more images as the patient takes one or more breaths and the gas washes out from the lungs. For example, the imaging system 50 may take images during an inhalation phase when the patient 22 takes in a breath, and/or an exhalation phase when the patient 22 breathes out. The images may be taken after a predetermined period and at a predetermined constant or variable spacing, such as 2 seconds, 5 seconds, 10 seconds, to about 30 seconds, to a total time of about 5 minutes after the breath-hold phase to allow the gas to be washed out from the patient's lungs. The imaging system 50 may take one or more high-dose, high-resolution scans, and one or more low-dose, lower resolution scans for dynamic data. The image acquisition and analysis may similar, for example, to those done in PET and SPECT. An example image acquisition set is described in the article by Marcos F Vidal Melo et al mentioned above.

Although the disclosure has been described in detail for the purpose of illustration based on what are currently considered to be the most practical and preferred aspects, it is to be understood that such detail is solely for that purpose and that the disclosure is not limited to the disclosed aspects, but, on the contrary, is intended to cover modifications and equivalent arrangements. For example, it is to be understood that the present disclosure contemplates that, to the extent possible, one or more features of any aspect can be combined with one or more features of any other aspect.

We claim:

1. A method for imaging an airspace of a lung of a patient, the method comprising:
    injecting a diagnostic contrast composition comprising a carrier fluid and a CT-active amount of a non-decaying gas-evolving liquid into a circulatory system of the patient wherein the gas-evolving liquid is sulfur hexafluoride, a perfluorocarbon, a bromoperfluorocarbon, or a combination of any thereof and has a vapor pressure sufficient to evolve as a gas from a circulatory system within the airspace of the lung of the patient;
    waiting a predetermined delay period after injection of the diagnostic contrast composition to allow the gas-evolving liquid to be delivered to the lungs by the circulatory system of the patient and to allow the gas to evolve into the airspace of the lung of the patient, wherein the predetermined delay period is less than about 5 minutes; and imaging at least a portion of the lung and the airspace of the lung using a CT or MR medical imager at the end of the predetermined delay period to produce at least a first contrast enhanced image of the at least the portion of the lung and the airspace of the lung, wherein imaging at least the portion of the lung and the airspace of the lung is performed during at least one of an inhalation phase, a breath-hold phase, and an exhalation phase.

2. The method of claim 1, further comprising imaging the at least the portion of the lung and the airspace of the lung to produce at least a second image of the at least the portion of the lung and the airspace of the lung after a predetermined period after injection of the diagnostic contrast composition, wherein the at least the second image is collected during at least one of a second inhalation phase, a second breath-hold phase, and a second exhalation phase.

3. The method of claim 1, wherein the gas-evolving liquid is a composition containing a sufficient quantity of atoms with an atomic number higher than 8 to provide a Hounsfield Unit measurement to affect an image in a CT imaging system.

4. The method of claim 1, wherein the diagnostic contrast composition further comprises at least one liquid or dissolved X-ray contrast imaging agent in the carrier fluid and wherein imaging at least the portion of the lung comprises computed tomographic imaging of the at least one liquid or dissolved X-ray contrast imaging agent in at least a portion of a tissue of the lung.

5. The method of claim 4, wherein at least one of the first image and a second image are a combined image of the at least one liquid or dissolved X-ray contrast imaging agent in the tissue of the lung and the gas evolved from the CT-active amount of the non-decaying gas-evolving liquid in the airspace of the lung.

6. The method of claim 1, wherein the non-decaying gas-evolving liquid is a perfluorocarbon.

7. The method of claim 1, wherein imaging at least the portion of the lung and the airspace of the lung using the CT or MR medical imager to produce at least the first image of the at least the portion of the lung and the airspace of the lung comprises taking one or more high-dose, high resolution first image of the at least the portion of the lung and the airspace of the lung.

8. The method of claim 7, wherein imaging at least the portion of the lung and the airspace of the lung using the CT or MR medical imager comprises taking at least one or more low-dose, low resolution second image of the at least the portion of the lung and the airspace of the lung.

9. The method of claim 8, further comprising dynamically analyzing data associated with the one or more high-dose, high resolution first image of the at least the portion of the lung and the airspace of the lung; and the at least one or more low-dose, low resolution second image of the at least the portion of the lung and the airspace of the lung.

10. The method of claim 9, wherein dynamically analyzing data comprises performing one or more of a pharmacokinetic analysis and a compartmental analysis of the airspace of the lung.

11. The method of claim 2, wherein the at least one second image comprises a plurality of images taken at a predetermined constant spacing after the end of the breath-hold phase.

12. The method of claim 11, wherein the plurality of images are taken at predetermined constant spacings of 2 second spacings, 5 second spacings, 10 second spacings, or up to 30 second spacings for a total time of about 5 minutes after the breath-hold phase.

13. The method of claim 2, wherein the at least one second image is taken at a predetermined variable spacing after the end of the breath-hold phase.

* * * * *

UNITED STATES PATENT AND TRADEMARK OFFICE
CERTIFICATE OF CORRECTION

| | |
|---|---|
| PATENT NO. | : 11,576,985 B2 |
| APPLICATION NO. | : 16/940601 |
| DATED | : February 14, 2023 |
| INVENTOR(S) | : Arthur Uber, III |

It is certified that error appears in the above-identified patent and that said Letters Patent is hereby corrected as shown below:

In the Specification

In Column 1, Line 8, delete "2017," and insert -- 2017, now abandoned, --, therefor.

In Column 1, Line 60, delete "flourine" and insert -- fluorine --, therefor.

In Column 13, Line 7, delete "Heptafluoro-N_propyl bromide" and insert -- Heptafluoro-N-propyl bromide --, therefor.

In Column 13, Line 34, delete "perfluoro-isobutane" and insert -- Perfluoro-isobutane --, therefor.

In Column 13, Line 39, delete "tetraflouride" and insert -- tetrafluoride --, therefor.

In Column 13, Line 48, delete "and or" and insert -- and/or --, therefor.

In Column 13, Line 49, delete "a" and insert -- as --, therefor.

In Column 16, Line 40, delete "similar," and insert -- be similar, --, therefor.

Signed and Sealed this
Eleventh Day of July, 2023

Katherine Kelly Vidal
*Director of the United States Patent and Trademark Office*